(12) United States Patent
Georgi et al.

(10) Patent No.: US 7,032,661 B2
(45) Date of Patent: Apr. 25, 2006

(54) METHOD AND APPARATUS FOR COMBINED NMR AND FORMATION TESTING FOR ASSESSING RELATIVE PERMEABILITY WITH FORMATION TESTING AND NUCLEAR MAGNETIC RESONANCE TESTING

(75) Inventors: Dan Georgi, Houston, TX (US);
Thomas Kruspe, Wienhausen (DE);
Matthias Meister, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/404,408

(22) Filed: Apr. 1, 2003

(65) Prior Publication Data

US 2004/0055745 A1 Mar. 25, 2004

Related U.S. Application Data

(63) Continuation-in-part of application No. 09/910,209, filed on Jul. 20, 2001, now Pat. No. 6,609,568.

(60) Provisional application No. 60/369,268, filed on Apr. 2, 2002, provisional application No. 60/406,082, filed on Aug. 26, 2002.

(51) Int. Cl.
*E21B 47/00* (2006.01)
(52) U.S. Cl. ............................. 166/250.01; 166/252.5; 73/152.31
(58) Field of Classification Search ........... 166/250.01, 166/252.5, 254.2, 250.02, 250.07, 260, 264; 702/12, 13; 73/152.31, 152.41, 152.52
See application file for complete search history.

(56) References Cited

U.S. PATENT DOCUMENTS

| 3,321,965 | A |   | 5/1967  | Johnson et al. |
|---|---|---|---|---|
| 4,622,643 | A | * | 11/1986 | Dotson ........................ 702/12 |
| 4,638,447 | A | * | 1/1987  | Odeh ........................... 702/12 |
| 4,868,751 | A | * | 9/1989  | Dogru et al. .................. 702/12 |
| 4,893,504 | A | * | 1/1990  | O'Meara et al. .......... 73/152.07 |
| 4,964,101 | A |   | 10/1990 | Liu et al. |
| 5,233,866 | A |   | 8/1993  | Desbrandes |
| 5,297,420 | A | * | 3/1994  | Gilliland et al. ............... 73/38 |

(Continued)

FOREIGN PATENT DOCUMENTS

EP 0490421 6/1992

(Continued)

*Primary Examiner*—Frank S. Tsay
(74) *Attorney, Agent, or Firm*—Madan, Mossman & Sriram, P.C.

(57) ABSTRACT

Formation testing, resistivity and NMR measurements are used concurrently to determine a relative permeability representative of a formation surrounding the borehole. A method and apparatus is provided for accurate determination of the relative permeability for a formation by measuring saturation levels in a region of interest determined from resistivity or NMR readings versus time during formation draw down pressure testing. The method and apparatus determines and effective permeability over time for various saturation levels to determine the relative permeability for the formation at each saturation level and also enables determination of the efficacy of utilizing completion fluids in the formation to increase formation productivity. The method and apparatus enables more accurate determination of effective permeability and the irreducible saturation level. The method and apparatus also provides for determination of whether a pad is sealed properly against a borehole wall and determines if a probe is clogged.

18 Claims, 4 Drawing Sheets

U.S. PATENT DOCUMENTS

| | | | |
|---|---|---|---|
| 5,299,453 A | * | 4/1994 | Sprunt et al. ............ 73/152.23 |
| 5,703,286 A | | 12/1997 | Proett et al. |
| 5,708,204 A | | 1/1998 | Kasap |
| 5,803,186 A | | 9/1998 | Berger et al. |
| 5,812,068 A | | 9/1998 | Wisler et al. |
| 5,936,405 A | | 8/1999 | Prammer et al. |
| 6,490,531 B1 | * | 12/2002 | Goglin et al. ................. 702/25 |
| 6,886,632 B1 | * | 5/2005 | Raghuraman et al. ... 166/252.4 |

FOREIGN PATENT DOCUMENTS

| | | |
|---|---|---|
| EP | 0520903 | 12/1992 |
| EP | 0698722 | 2/1996 |

* cited by examiner

Fig. 4

# METHOD AND APPARATUS FOR COMBINED NMR AND FORMATION TESTING FOR ASSESSING RELATIVE PERMEABILITY WITH FORMATION TESTING AND NUCLEAR MAGNETIC RESONANCE TESTING

CROSS REFERENCE TO RELATED APPLICATIONS

This patent application is a continuation in part of and claims priority from U.S. patent application Ser. No. 09/910,209 entitled Apparatus and Method for In Situ Analysis of Formation Fluids by Krueger et al. filed on Jul. 20, 2001, now U.S. Pat. No. 6,609,568 which is incorporated herein by reference in its entirety. This application is related to and claims priority from U.S. patent application Ser. No. 60/369,268 entitled, "Combined NMR and Formation Testing" by Georgi et al. filed on Apr. 2, 2002,which is incorporated herein by reference in its entirety. This application is related to and claims priority from U.S. patent application Ser. No. 60/406,082 entitled, "A Method and Apparatus for Combined NMR and Formation Testing For Assessing Relative Permeability with Formation Testing and Nuclear Magnetic Resonance Testing" by Georgi et al. filed on Aug. 26, 2002, which is incorporated herein by reference in its entirety.

BACKGROUND OF THE INVENTION

1. Field of the Invention

The present invention relates generally to the field of formation testing over time during or after drilling and in particular to the concurrent or sequential attainment of nuclear magnetic resonance (NMR) data or resistivity data during formation testing for measuring the saturation of the formation over time to determine the relative permeability for a hydrocarbon bearing formation.

2. Summary of the Related Art

To obtain hydrocarbons such as oil and gas, boreholes are drilled by rotating a drill bit attached at a drill string end. A large proportion of the current drilling activity involves directional drilling, i.e., drilling deviated and horizontal boreholes to increase the hydrocarbon production and/or to withdraw additional hydrocarbons from the earth's formations. Modem directional drilling systems generally employ a drill string having a bottomhole assembly (BHA) and a drill bit at an end thereof that is rotated by a drill motor (mud motor) and/or by rotating the drill string. A number of downhole devices placed in close proximity to the drill bit measure certain downhole operating parameters associated with the drill string. Such devices typically include sensors for measuring downhole temperature and pressure, azimuth and inclination measuring devices and a resistivity-measuring device to determine the presence of hydrocarbons and water. Additional down-hole instruments, known as logging-while-drilling (LWD) tools, are frequently attached to the drill string to determine the formation geology and formation fluid conditions during the drilling operations.

Drilling fluid (commonly known as the "mud" or "drilling mud") is pumped into the drill pipe to rotate the drill motor, provide lubrication to various members of the drill string including the drill bit and to remove cuttings produced by the drill bit. The drill pipe is rotated by a prime mover, such as a motor, to facilitate directional drilling and to drill vertical boreholes. The drill bit is typically coupled to a bearing assembly having a drive shaft, which in turn rotates the drill bit attached thereto. Radial and axial bearings in the bearing assembly provide support to the radial and axial forces of the drill bit.

Boreholes are usually drilled along predetermined paths and the drilling of a typical borehole proceeds through various formations. The drilling operator typically controls the surface-controlled drilling parameters, such as the weight on bit, drilling fluid flow through the drill pipe, the drill string rotational speed and the density and viscosity of the drilling fluid to optimize the drilling operations. The downhole operating conditions continually change and the operator must react to such changes and adjust the surface-controlled parameters to optimize the drilling operations. For drilling a borehole in a virgin region, the operator typically has seismic survey plots which provide a macro picture of the subsurface formations and a pre-planned borehole path. For drilling multiple boreholes in the same formation, the operator also has information about the previously drilled boreholes in the same formation.

Typically, the information provided to the operator during drilling includes borehole pressure and temperature and drilling parameters, such as Weight-On-Bit (WOB), rotational speed of the drill bit and/or the drill string, and the drilling fluid flow rate. In some cases, the drilling operator also is provided selected information about the bottom hole assembly condition (parameters), such as torque, mud motor differential pressure, bit bounce and whirl etc.

Downhole sensor data are typically processed downhole to some extent and telemetered uphole by sending a signal through the drill string, or by mud-pulse telemetry which is transmitting pressure pulses through the circulating drilling fluid. Although mud-pulse telemetry is more commonly used, such a system is capable of transmitting only a few (1–4) bits of information per second. Due to such a low transmission rate, the trend in the industry has been to attempt to process greater amounts of data downhole and transmit selected computed results or "answers" uphole for use by the driller for controlling the drilling operations.

Commercial development of hydrocarbon fields requires significant amounts of capital. Before field development begins, operators desire to have as much data as possible in order to evaluate the reservoir for commercial viability. Despite the advances in data acquisition during drilling using the MWD systems, it is often necessary to conduct further testing of the hydrocarbon reservoirs in order to obtain additional data. Therefore, after the well has been drilled, the hydrocarbon zones are often tested with other test equipment.

One type of post-drilling test involves producing fluid from the reservoir, shutting-in the well, collecting samples with a probe or dual packers, reducing pressure in a test volume and allowing the pressure to build-up to a static level. This sequence may be repeated several times at several different depths or point within a single reservoir and/or at several different reservoirs within a given borehole. One of the important aspects of the data collected during such a test is the pressure build-up information gathered after drawing the pressure down. From these data, information can be derived as to permeability, and size of the reservoir. Further, actual samples of the reservoir fluid must be obtained, and these samples must be tested to gather Pressure-Volume-Temperature and fluid properties such as density, viscosity and composition.

A more recent system is disclosed in U.S. Pat. No. 5,803,186 to Berger et al (the '186 patent). The '186 patent provides a MWD system that includes use of pressure and resistivity sensors with the MWD system, to allow for real time data transmission of those measurements. The '186 device allows obtaining static pressures, pressure build-ups, and pressure draw-downs with the work string, such as a drill string, in place. Also, computation of permeability and other reservoir parameters based on the pressure measurements can be accomplished without pulling the drill string.

The system described in the '186 patent decreases the time required to take a test when compared to using a wireline. However, the '186 patent does not provide an apparatus for improved efficiency when wireline applications are desirable. A pressure gradient test is one such test wherein multiple pressure tests are taken as a wireline conveys a test apparatus downward through a borehole. The purpose of the test is to determine fluid density in-situ and the interface or contact points between gas, oil and water when these fluids are present in a single reservoir. Another apparatus and method for measuring formation pressure is described in U.S. Pat. No. 5,233,866 issued to Robert Desbrandes.

Various means of estimating permeability from Darcy's law have been proposed for formation testing are well known in the art. For example, U.S. Pat. No. 5,303,775 by Michaels describes a Reservoir Characterization Instrument that enables an operator to determine formation properties from formation testing measurements of pressure, volume and temperature made in situ down hole in the well bore. It is well known that absolute formation permeability and fluid mobility determinations can be derived from pressure, volume and temperature and viscosity measurements. Permeability is useful in determining potential productivity of a formation adjacent a well bore. It is also known that downhole NMR tools also enable an operator to determine formation parameters of interest, including permeability from in situ NMR measurements. Generally, these methods do not distinguish between absolute, effective and relative permeability.

These known methods for determining the surrounding formation permeability do not, however, take into account the saturation level of the surrounding formation or determining the relative permeability for the formation. The absolute permeability represents the permeability for a fluid with only a single fluid in the formation. Since most formations contain more than one fluid, it is more pertinent to determine the permeability of a fluid in the presence of another fluid at a given saturation level, i.e., the relative permeability. It is the relative permeability that determines the actual productivity of a formation surrounding a well. Thus, there is a need for a method and apparatus for determining the saturation level of the surrounding formation and the relative permeability for the surrounding formation.

SUMMARY OF THE INVENTION

The present invention analyzes a formation adjacent a wellbore. Formation testing, resistivity and NMR measurements are performed concurrently to determine a relative permeability, which is representative of the formation surrounding the borehole. The present invention provides a method and apparatus for accurate determination of the relative permeability for a formation by measuring saturation levels in a region of interest determined from NMR or resistivity readings versus time during formation draw down pressure testing. The present invention determines effective permeability over time for various saturation levels to determine the relative permeability for the formation at each saturation level. In another aspect, the present invention also enables determination of the efficacy of utilizing completion fluids in the formation to increase formation productivity. In another aspect, the present invention enables more accurate determination of effective permeability. In another aspect of the invention, the present invention enables determination of the irreducible saturation level. In another aspect of the invention, the present invention enables determination of efficacy of using completion fluids in a formation. In another aspect of the invention, a method and apparatus are provided to determine whether a pad is sealed properly against a borehole wall. In another aspect of the invention, a method and apparatus are provided to determine if a fluid passage for pumping fluid from the formation is clogged. Other features and advantages will be evident from the following description.

DETAILED DESCRIPTION OF A PREFERRED EMBODIMENT

Figure 1:
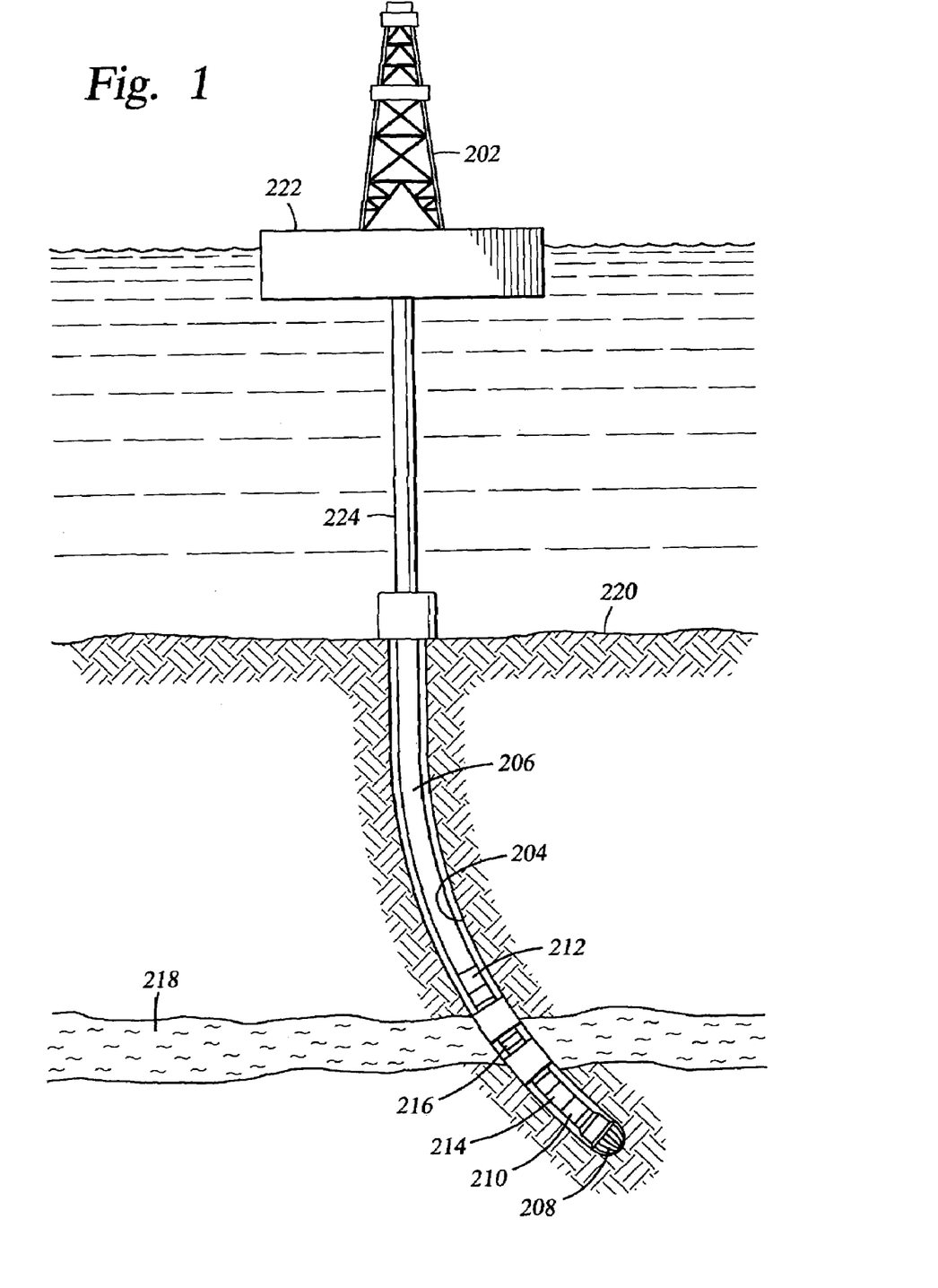
FIG. 1 is an illustration of a preferred embodiment of the present invention deployed in a borehole in a monitoring while drilling operation for determination of the relative permeability of the formation surrounding the borehole.

The present invention enables concurrent or simultaneous NMR saturation measurements and formation test measurements to determine the relative permeability of a formation, thereby significantly benefiting oil field analysts trying to ascertain the productivity a well. FIG. 1 illustrates a preferred embodiment of the present invention deployed in a bottom hole assembly.

Turning now to FIG. 1, FIG. 1 is a drilling apparatus according to one embodiment of the present invention. A typical drilling rig 202 with a borehole 204 extending there from is illustrated, as is well understood by those of ordinary skill in the art. The drilling rig 202 has a work string 206, which in the embodiment shown is a drill string. The drill string 206 has attached thereto a drill bit 208 for drilling the borehole 204. The present invention is also useful in other types of work strings, and it is useful with a wireline, jointed tubing, coiled tubing, or other small diameter work string such as snubbing pipe. The drilling rig 202 is shown positioned on a drilling ship 222 with a riser 224 extending from the drilling ship 222 to the sea floor 220. However, any drilling rig configuration such as a land-based rig may be adapted to implement the present invention.

If applicable, the drill string 206 can have a downhole drill motor 210. Incorporated in the drill string 206 above the drill bit 208 is a typical testing unit, which can have at least one sensor 214 to sense downhole characteristics of the borehole, the bit, and the reservoir, with such sensors being well known in the art. A useful application of the sensor 214 is to determine direction, azimuth and orientation of the drill string 206 using an accelerometer or similar sensor. The BHA also contains the formation test apparatus 216 of the present invention, which will be described in greater detail hereinafter. A telemetry system 212 is located in a suitable location on the work string 206 such as above the test apparatus 216. The telemetry system 212 is used for command and data communication between the surface and the test apparatus 216.

In a preferred embodiment, to determine relative permeability or mobility, the present invention quantifies the fluid saturations in the pore space with NMR or resistivity as the reservoir pressure and effective permeability and mobility are determined. Mobility is equal to the permeability divided by the viscosity. There are several methods for determining viscosity from NMR data as taught in U.S. Pat. No. 6,084,408 by Georgi, et al. One can determine the intrinsic $T_2$ and determine viscosity from a correlation as taught by Vinejar et. al., wherein T2 is proportional to absolute temperature/viscosity. One can also use NMR to determine viscosity using the Einstein relationship, V is proportional to absolute temperature/diffusivity. The NMR determines viscosity, which is used to convert the mobility to permeability.

The saturation level in front of the probe changes as the fluid is pumped from the formation. These steps are repeated until the mobile fluid saturation and the effective permeability have been determined at each saturation level. The result is a series of effective permeability and mobile fluid saturation determinations at varying saturation levels. The process is stopped when the water saturation level no longer decreases. At this level, the irreducible fluid saturation has been reached.

Figure 4:
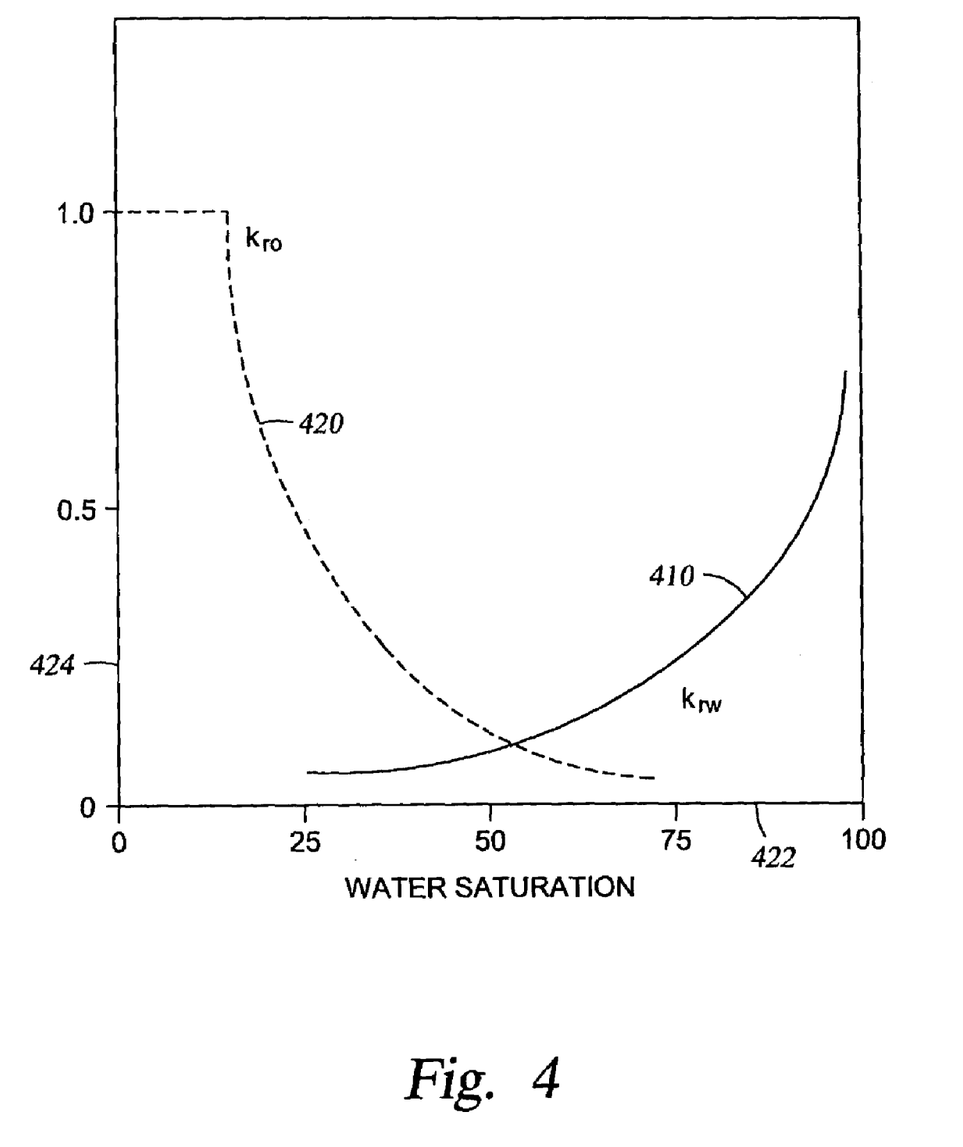
FIG. 4 is an illustration of a relative permeability curve for water and oil for water/oil saturation levels which vary between 0 and 100 per cent, showing the relative permeability, as a percentage of absolute permeability attainable for water and oil at a continuum of water/oil saturation levels.

FIG. 4 is an illustration of the relative permeability of water 410 and for oil 420 at given saturations of water and oil. The relative permeability is shown as a fraction of $K_{effective}/K_{absolute}$, where $K_{effective}$ is approximately equal to $K_{absolute}$ for water when the water saturation 422 approaches 100% and $K_{effective}$ is approximately equal to $K_{absolute}$ for oil when the oil saturation approaches 100%. As shown in FIG. 4, the relative permeability of oil, $K_{ro}$ varies from approximately $K_{absolute}$ to approximately 0 as the water saturation increases from approximately 0 to 100 per cent. Similarly, the relative permeability of water, $K_{rw}$ varies from approximately $K_{absolute}$ to approximately 0 as the oil saturation increases from approximately 0 to 100 per cent.

Standard formation testing is well known in the art. Pressure testing, however, cannot measure flow velocity in the formation. Such tests are limited to measuring fluid flow coming into the pressure testing tool. The present invention determines fluid velocity in or near the NMR or resistivity sensitive volume and combines this information with the estimated pressure gradient across the NMR/resistivity sensitive volume to determine the permeability in the sensitive volume.

NMR can be used to determine the velocity of a fluid similar to diffusion measurement where the magnetic spins are moved erratically inside the formation from one position in the field gradient, changing the Larmor frequency of the spins to detect motion of spins. Such known NMR techniques are used, for example, to detect blood flow in the human body. The NMR fluid velocity determination is used to correct the pressure test derived fluid velocity.

Additional sensors are provided in test apparatus 216 with the NMR and formation testing measurement devices and measurements comprising resistivity, near infrared refractometry, viscosity sensors, dielectric sensors and optical spectroscopy. These additional sensors are well known in the art and are not shown in detail in the figures for simplicity. A processor is provided in the tool downhole for calculation, correlation and correction of the various test parameters and measurements. A neural net trained by a test base of correlated formation properties is provided to infer a unknown formation property from other known, measured or estimated formation properties.

The present invention uses the determination of the fluid velocity for the pore space to derive a permeability figure, which is more accurate than the NMR determined permeability. NMR permeabilities are based on pore space surface area and pore space distribution. Alone, NMR cannot determine tortuosity that is how the pore space is connected. A multiple inter-echo time, $T_e$ or multiple wait time, $T_w$ NMR experiment is provided by the present invention distinguish between a low viscous and high viscous fluid in the pore space, e.g., water versus oil, or heavy oil and light oil and distinguish between fluids or phases, e.g., water, oil, gas by a NMR experiment using multiple relaxation times, $T_1$. The present invention also determines whether formation fluid or well bore fluid is taken into the tool during draw-down testing.

The present invention enables determination of relative permeability. Relative permeability characteristics are important for understanding the displacement of hydrocarbons at any stage of production. Darcy's law as originally developed applies to a porous medium, which is fully saturated with a single phase fluid. In the typical reservoir, however, two or more fluids are usually present so it is necessary to introduce the concept of effective permeability. In the definition of effective permeability each fluid phase is considered to be completely independent of the other fluids. Thus Darcy's law can be applied to each fluid individually. The absolute or specific permeability is the permeability with only one fluid present at 100 percent saturation of the pore space. The effective permeability is the permeability to one fluid phase in the presence of another fluid phase. The effective permeability is the conductivity of each phase at a specific saturation of the other phase.

In addition to being influenced by the saturation of the other fluids, effective permeability is also a function of the rock wetting characteristics and the pore geometry. Relative permeability is defined as the ratio of effective permeability of a fluid at a given saturation to the specific permeability of that fluid at 100% saturation.

$$\text{Relative Permeability} = \frac{\text{Effective Permeability}}{\text{Specific Permeability}}$$

The relative permeability ratio is reported as a fraction or percentage. In relative permeability tests an effective permeability is often used as a base permeability. Rather than always using the permeability when only one fluid is present at 100% saturation as the base value, the permeability of one fluid when the other fluid is immobile is often used e.g. the permeability to oil at irreducible water saturation (Ko@ Swir). It is important to ensure a common base is used when evaluating or comparing data.

Relative permeability is influenced by the distribution of fluids in the rock, the saturation history and the wettability of the rock. Saturation history influences the data, therefore tests must follow reservoir history. Rock wettability influences the fluid distribution and therefore flow within the reservoir. Samples with non-representative wettability would give non-representative data.

Imbibition relative permeability describes the relative permeability characteristics when the wetting phase is increasing, e.g., water flooding in a water wet reservoir. Drainage relative permeability describes the relative permeability characteristics when a non-wetting phase is increasing e.g. gas displacing oil during primary recovery, or oil displacing water during initial oil migration into a reservoir. Relative permeability characteristics indications of the distribution of fluid within porous media can be deduced from relative permeability data. As non-wetting oil migrates into the reservoir which is water filled it first displaces water from the larger pores. This displacement results in a rapid decline in the relative permeability to water. As the oil saturation continues to increase the remaining water occupies successively smaller pores characterized by a rapid rise in the relative permeability to oil.

Secondary imbibition of water during water flooding results in a different set of relative permeability curves. Assuming a water wet situation oil occupies the center of the large pores with water existing as a thin film around the grains and occupying only the smallest pores not originally invaded by oil. At this stage the water is immobile and has little or no effect on the flow of oil and the oil relative permeability at this stage is 100%. The water saturation prior to water flood is immobile and the relative permeability to water is zero. Water flooding results in water flow initially through the large pores and subsequently through smaller pores as the oil saturation decreases. The water saturation continues to increase as the oil saturation decreases down to a residual saturation. At this stage the residual oil remains trapped in the center of the pores. As the oil is no longer mobile, the relative permeability to oil becomes zero whereas the relative permeability to water reaches its maximum. This value will not reach 100% due to the residual oil saturation restricting flow so the permeability to water at this stage is an effective permeability.

In an oil wet reservoir oil is adhering to the grain surfaces and water exists as trapped globules in the center of pores or in the smallest pores which were not invaded by oil during the initial oil migration into the reservoir. In this situation the relative permeability to oil will be lower as the flow of oil will be impeded by the oil wet nature of the rock holding back the oil. Inversely the water relative permeability will be higher than in a water-wet situation.

Figure 2:
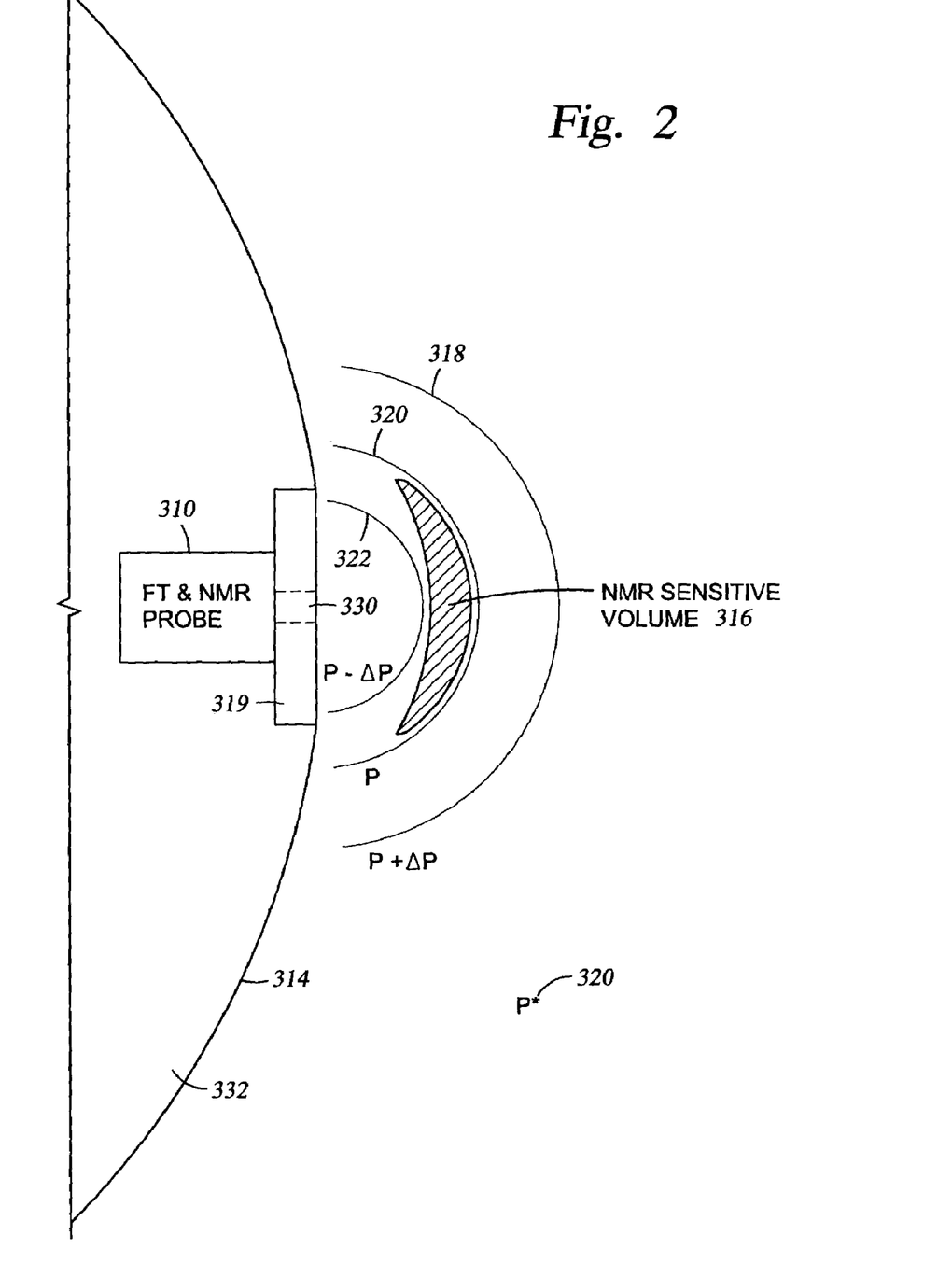
FIG. 2 is an illustration of a pad mounted saturation level measuring tool comprising NMR or resistivity device and formation testing probe deployed in a well bore for conducting resistivity NMR and formation testing in a preferred embodiment of the present invention for determination of the relative permeability of the formation surrounding the bore hole.

Turning now to FIG. 2, the present invention provides a pad mountable saturation determining device, e.g., an NMR or resistivity device and a formation testing tool mounted in an extensible probe and pad device on either a logging while drilling tool or a wire line formation tester probe assembly such as the Baker Atlas Reservoir Characterization Instrument (RCI). RCI is detailed in U.S. Pat. No. 5,303,775 by Michaels et al., which is incorporated by reference in its entirety. A monitoring while drilling formation tester extensible probe assembly is detailed in U.S. patent application Ser. No. 09/910,209 cited above. In either configuration, wire line or logging while drilling, the present invention provides for relative permeability determination over time derived from formation and pressure draw down testing over time combined with NMR or resistivity saturation measurements over time to determine relative permeability. As shown in FIG. 2, in a preferred embodiment, the resistivity/NMR saturation measurement is confined to an area associated with a localized resistivity/NMR region of interest 316 close to the borehole 332 within a few radii of the formation test tool probe, that is, the radius of the internal passage or orifice provided for ingress of formation fluid 330 and egress of completion fluid through the borehole wall 314 to the formation. The probe 310 extends from the downhole tool to press and seal the probe face 319 against the borehole wall 314. Formation fluid is extracted from the borehole through the probe 310. Completion fluid is injected into the formation through the probe 310. The provision of adjacent formation testing and NMR equipment in the same down hole tool enables concurrent determination of saturation level and absolute permeability with NMR (Coates-Timur equation) data and mobility data from draw down-buildup analysis performed by the formation testing equipment.

The present invention also provides a method and apparatus for determining absolute "end-point" permeability for either oil or water when the area being investigated, that is, the area within roughly 3 probe radii of the inner probe orifice is either 100 % water or oil saturated, for example, 100 per cent water based mud filtrate. The present invention also determines the relative permeability for oil for a plurality of water saturation levels. Having both formation testing and NMR measured permeabilities enables comparison of the measurements and refinement of the parameters in the Coates-Timur equation or the $T_2$ Geometric Mean based NMR permeability based on the formation testing calculated permeability. The primary advantage of the present invention, however, is the ability to determine the relative permeability for the formation based on the calculation of saturation levels over time from the NMR measurements or resistivity measurements and calculations of effective permeability over time to determine the relative permeability for the formation at given saturation levels.

Critical gas and condensate saturations, residual oil saturation, trapped oil and gas saturations, and irreducible water saturation are the most frequently encountered end-points. Critical saturation, whether gas or condensate, refers to the saturation at which a phase first becomes mobile. Trapped gas, residual oil, and irreducible water saturations all refer to the remaining saturation of a phase after extensive displacement has occurred.

This statement is consistent with the interpretation that "end-point" saturations refer to the saturations in a rock with two phases where one phase becomes immobile. For example, as the water saturation increases eventually oil will no longer flow and the residual oil saturation (Sro) when the oil no longer flow and only water flows would be the "end-point" oil saturation. On the other hand when the water saturation becomes small and approaches the irreducible water saturation, water will cease to flow and we would be at the irreducible water saturation "end-point."

Figure 3:
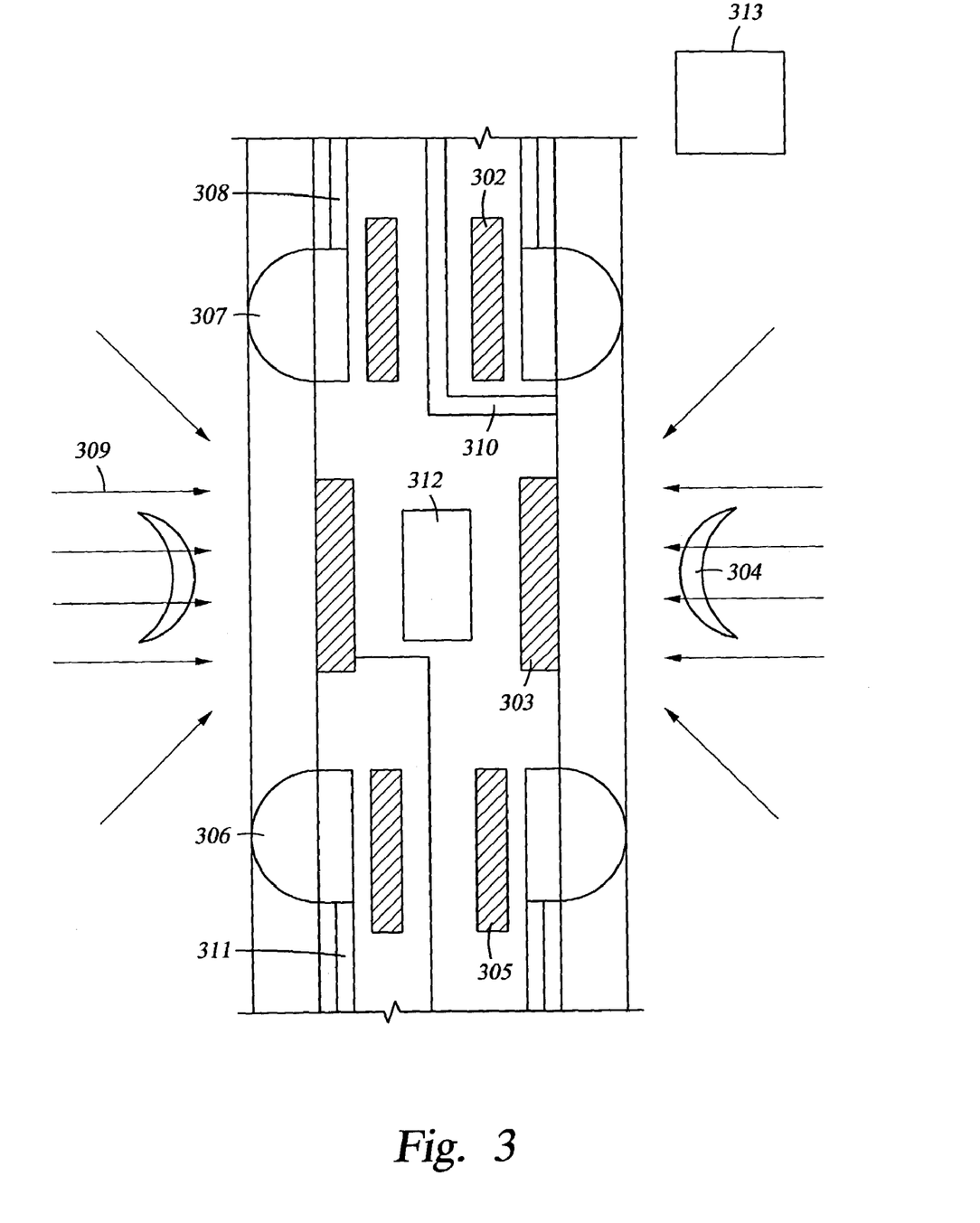
FIG. 3 is an illustration of an alternative embodiment of the present invention comprising a dual packer tool combined with a formation testing, resistivity and NMR measurement tool for determination of the relative permeability of the formation surrounding the bore hole.

FIG. 3 illustrates an alternative embodiment of the present invention using a dual packer tool combined with a formation testing and a NMR measurement tool for determination of the relative permeability of the formation surrounding the borehole. Turning now to FIG. 3, a dual packer formation test tool combined with an NMR sensor displayed. A multi-sensor apparatus pack 312 including a resistivity measuring device is located inside of the tool. An intelligent acquisition and completion system 313 is located on the surface for receiving input from the tool and processing the inputs to make determinations about further acquisition and actions in the borehole or formation. A set of hydraulic packers 307 and 306 engage the borehole wall and seals off an area of the annulus through which formation fluid may enter the tool. The suction line 310 of the formation tester enable formation fluid or wellbore fluid to enter the tool. A zone of interest 304 is set up by the NMR permanent magnets 301 and 305 and NMR RF antenna 303. A hydraulic line of packer 1 308 and hydraulic line of packer 2 311 activate the packers to seal off an area of the annulus between packer 1 and packer 2.

In a preferred embodiment, fluid velocities and saturation levels are determined directly with the resistivity tool in the multi-sensor pact 312 or NMR probe in the NMR sensitive volume using NMR measurement techniques combined with estimates of the pressure gradient across the NMR sensitive volume to determine a relative permeability for a given saturation level in the sensitive volume. The pressure gradient calculation utilizes absolute permeability derived from mobility data from the formation rate analysis converting the formation test-based mobility into permeability. This is achieved by using the NMR or resistivity saturation data, as discussed below.

The acquisition and processing of NMR data for the calculation of a parameter of interest for a formation are well known in the art. In a preferred embodiment, NMR parameters, T1 and T2 are obtained with dual or multiple TE and/or dual or multiple TW NMR data and/or diffusion data are used to determine viscosity and convert the formation test determined mobility to a relative permeability determination. In a preferred embodiment, the relative permeability (k) or mobility (k/µ) (µ=viscosity) is calculated by determining a saturation value for a location in a formation; measuring a pressure value for the location in the formation; and determining the relative permeability for the formation from the saturation value and the pressure value at the location in the formation. In a preferred embodiment, NMR or resistivity measurements are used to monitor saturation of the wetting phase, that is, water in the formation which measuring the pressure in the formation as different saturations. The NMR measurement also yields viscosity.

The NMR or resistivity measurements are made during the same down hole pass or in a separate down hole pass as the pass for pressure testing. The NMR measurements enable estimation of saturation levels in the formation and help determine relative permeability. In an alternative embodiment, resistivity measurements are used to obtain an estimate of saturation levels in the formation location being pressure tested. Resistivity or dielectric means are used for assessing saturation of the formation.

In a preferred embodiment, the fluid saturation levels in the NMR region of interest in the formation pore space are determined using NMR and concurrently the formation mobility is determined from formation or reservoir pressure testing using analysis methods such as discussed in U.S. patent application Ser. No. 09/910,209 file on Jul. 20, 2001, entitled "Apparatus and Method for In Situ Analysis of Formation Fluids" by Krueger et al..

As formation fluid is pumped from the formation during pressure testing, water that had invaded the formation is pumped from the formation, thereby reducing the water saturation level. Correspondingly, the oil saturation level increases over time as pumping continues. Thus, over time, the water saturation level in front of the probe changes as the water is depleted. The declining water saturation level is monitored with the NMR while pumping water from the formation as the water and oil saturation changes over time.

In a preferred embodiment, the present invention injects a fluid having a known viscosity into the formation and uses NMR or resistivity measurements to determine saturation levels in the formation, measures pressure responses, injects more fluid into the formation to change the saturation level in the formation, uses NMR or resistivity to determine saturation levels in the formation and determines relative permeability or mobility there from.

The determination of the mobility is repeated over time using the draw down-buildup determination with the formation test tool. These two steps are repeated until one has determined the mobile fluid saturation level and the effective permeability at each NMR or resistivity measured saturation level. The process is complete when the water saturation does not decrease any more, or after a reasonable period of time or has leveled off, thereby arriving at the "true" irreducible fluid saturation level. This irreducible fluid saturation level is the water saturation level that will not decrease with further pumping from the formation. The irreducible water saturation level is important to determining the productivity for a formation. The irreducible water saturation level may be improved by injection of completion fluid, as discussed below.

These saturation and effective mobility data versus time enable plotting a relative permeability curve as shown in FIG. 4 from the calculated data points. If the drilling mud is water based this process will provide $K_{ro}$, the relative permeability of oil at various water saturation levels as drilling mud is pumped to or from the formation. In a preferred embodiment, Enperforming a draw down-buildup test while the fluid saturations as observed with NMR or resistivity have become stabilized, computes an "end-point" relative permeability.

The efficacy of using completion fluid in the formation is determined by the present invention. In a preferred embodiment, completion fluid is pumped into the formation until maximum saturation is achieved. By pumping the completion fluid back out of the formation, the present invention can monitor changes in wettability using the NMR data to assess the potential efficacy of using completion fluid to increase production in the well. For example, if a lower irreducible fluid saturation level is reached after injection and removal of completion fluid, this indicates that the formation would probably benefit from the use of completion fluid. The present invention also injects fluid having known NMR or resistivity properties into the formation to be used as a tracer to track movement of the injected fluid.

The present invention also determines the wettability of the formation, that is, the affinity of the formation for water or oil. Completion fluids contain wettability altering fluids (to render the formation water wet) are pumped into the formation is then pumped out, using the combination of draw down testing and NMR testing to determine whether the irreducible saturation is lower after injection and removal of the completion fluid than the irreducible saturation level prior to injection of the completion fluid.

The present invention also determines the integrity of the seal between the wellbore wall and the tool probe pad. In a typical wire line environment, the wellbore accumulates a mud cake on the wellbore wall from 1–3 millimeters thickness. This mud cake may prevent or inhibit sealing of the extensible probe and pad with the wellbore wall. The present invention determines the NMR fluid velocity and compares it to the theoretical model based fluid velocity for the formation for the drawdown rate being used. If the measured and theoretical velocities match, then a good probe seal is indicated. If the measured velocity is less than the theoretical velocity, then a leak in the probe seal is indicated. The present invention also indicates when the probe is clogged during draw down testing by immediately detecting when there is no flow velocity in the formation even though there may be a pressure build up in the tool.

NMR data is taken with and without the pressure gradient in the region of interest to determine what fluid is moveable and what fluid is not moveable. The NMR experiment parameters chosen to track only the irreducible fluid, the fluid that stays in place for a relatively long period of time, i.e., 500 msec. The present invention also injects fluids mixed with hyper-polarized elements such as Zenon, Argon or Helium gas or any other NMR traceable element. These hyper-polarized elements increase the NMR signal and response thereby increasing the signal to noise ratio for the NMR measurements. The present invention also provides data for an intelligent completion system. Data regarding whether fluids or solids are moved in the formation. For example, movement of sand in the formation which is undesirable in a production situation would be of particular interest to an intelligent completion system.

While a preferred embodiment of the present invention has been shown by way of illustration, it is for example purposes only and not intended to define or limit the scope which is defined by the following claims

What is claimed is:

1. A downhole tool comprising:
   a device associated with the downhole tool that determines permeability for a location in a formation;
   a device that determines a saturation level for the location in the formation wherein the device that determines the saturation level for the location in the formation comprises a nuclear magnetic resonance (MNR) tool; and
   a processor that determines a relative permeability for the location in the formation from the permeability and the saturation.

2. A downhole tool comprising:
   a device associated with the downhole tool that determines permeability for a location in a formation;
   a device that determines a saturation level for the location in the formation;
   a processor that determines a relative permeability for the location in the formation from the permeability and the saturation; and
   an injector that injects a fluid into the formation for determining an irreducible saturation level for the location in the formation.

3. A method for determining a relative permeability for a location in a formation comprising:
   determining a saturation value for a location in a formation;
   determining a permeability value for the location in the formation;
   determining a relative permeability for the formation from the saturation value and the permeability value at the location in the formation;
   performing a nuclear magnetic resonance (NMR) measurement at the location in the formation;
   determining a viscosity of a fluid in the formation from the NMR measurement; and
   computing the permeability from a viscosity of the fluid.

4. A method for determining a relative permeability for a location in a formation comprising:
   determining a saturation value for a location in a formation;
   determining a permeability value for the location in the formation;
   determining a relative permeability for the formation from the saturation value and the permeability value at the location in the formation; and
   comparing a mobility for the location in the formation to an NMR permeability to adjust an NMR parameter.

5. A method for calculating formation productivity comprising:
   deploying a nuclear magnetic resonance (NMR) device in a formation;
   measuring mobility for a location in the formation;
   measuring a saturation level for the location in the formation; and
   calculating a relative permeability from the measured mobility and the saturation level at the location in the formation.

6. The method of claim 5, wherein calculating relative permeability further comprises converting the mobility to the relative permeability using viscosity data.

7. The method of claim 5, further comprising:
   pumping fluid from the formation; and
   measuring the mobility and the saturation for the fluid to calculate a relative permeability for the location in the formation at various saturation values until the saturation values substantially stops changing during the pumping of the fluid from the formation.

8. The method of claims 7, further comprising:
   calculating an irreducible saturation level for the location in the formation.

9. The method of claim 8, further comprising:
   injecting a fluid into the formation; and
   recalculating the irreducible saturation level.

10. The method of claim 8, further comprising:
    injecting a fluid into the formation; and
    calculating a moveable saturation level for the location in the formation.

11. The method of claim 5, further comprising:
    injecting a fluid containing a hyper-polarized agent into the formation to increase a signal to noise ratio for NMR measurements associated with the formation.

12. The method of claim 5, further comprising:
    pumping a fluid from the formation through a flow line; and
    monitoring a flow rate in the flow line to determine when the flow line is clogged.

13. The method of claim 5, further comprising:
    measuring a fluid flow rate in a probe; and
    comparing the measured fluid flow rate to a hypothetical fluid flow rate for a pressure gradient created by the probe to determine if the probe is sealed with a borehole wall.

14. The method of claim 5, further comprising:
    providing at least one of mobility, permeability and saturation to an intelligent completion system at a surface location.

15. The method of claim 5, further comprising:
    obtaining a fluid from the formation in a probe; and
    testing fluid in the probe to determine if the fluid is a wellbore fluid or formation fluid.

16. The method of claim 5, further comprising:
    determining an end point permeability for at least one of oil and water.

17. The method of claim 5, further comprising:
    measuring resistivity for the location in the formation;
    monitoring the fluid saturation level; and computing a relative permeability for the location in the formation.

18. A method for determining relative permeability of a formation location comprising:
  injecting a fluid having a known viscosity into the formation location;
  determining a saturation level for the formation location;
  measuring pressure responses in the formation location;
  injecting additional fluid into the formation location to change the saturation level in the formation location;
  determining a change in the saturation level for the formation location;
  and determining a relative permeability for the formation location from the change in the saturation level.

* * * * *